(12) United States Patent
Dudziak et al.

(10) Patent No.: US 7,449,093 B2
(45) Date of Patent: Nov. 11, 2008

(54) DEVICE AND METHOD FOR PREPARATIVE ELECTROPHORESIS

(76) Inventors: Gregor Dudziak, Max-Franz-Str. 4, 53177 Bonn (DE); Andreas Nickel, Lütge Varney 10, 58300 Wetter (DE); Martina Mutter, Hacketäuer Str. 52, 51063 Köln (DE); Kerstin Baumarth, Friedhofstr. 12, 42277 Wuppertal (DE)

( * ) Notice: Subject to any disclaimer, the term of this patent is extended or adjusted under 35 U.S.C. 154(b) by 710 days.

(21) Appl. No.: 10/714,047

(22) Filed: Nov. 13, 2003

(65) Prior Publication Data
US 2005/0072675 A1    Apr. 7, 2005

(30) Foreign Application Priority Data
Nov. 18, 2002 (DE) ............................ 102 53 483

(51) Int. Cl.
*G01N 27/447* (2006.01)
*G01N 27/453* (2006.01)

(52) U.S. Cl. .................. 204/450; 204/600; 210/637

(58) Field of Classification Search .............. 204/600; 210/637, 642, 644, 649, 651, 652, 653, 655, 210/650
See application file for complete search history.

(56) References Cited

U.S. PATENT DOCUMENTS

| | | | | |
|---|---|---|---|---|
| 3,989,613 A | | 11/1976 | Gritzner | 204/180 |
| 4,043,895 A | * | 8/1977 | Gritzner | 204/600 |
| 4,043,896 A | * | 8/1977 | Ahlgren | 204/637 |
| 4,180,451 A | | 12/1979 | McRae | 204/301 |
| 4,243,507 A | | 1/1981 | Martin et al. | 204/180 |
| 4,608,147 A | | 8/1986 | Clad | 204/180 |
| 4,758,320 A | * | 7/1988 | Sanchez et al. | 204/544 |
| 5,087,338 A | * | 2/1992 | Perry et al. | 435/173.2 |
| 6,270,672 B1 | | 8/2001 | Turecek et al. | 210/645 |
| 2003/0019753 A1 | * | 1/2003 | Ogle et al. | 204/548 |

FOREIGN PATENT DOCUMENTS

| | | |
|---|---|---|
| DE | 33 37 669 | 5/1985 |
| DE | 36 26 953 | 3/1987 |
| EP | 0 369 945 | 5/1990 |
| WO | WO 94/11728 | 5/1994 |

OTHER PUBLICATIONS

Galier et al., *J. Membr. Sci.* 194 (2001) 117-133.

* cited by examiner

*Primary Examiner*—Kaj K Olsen

(57) ABSTRACT

Method and appliance for carrying out membrane electrophoresis using microfiltration or ultrafiltration membranes, wherein the electroosmotic flow which develops in the membrane pores is reduced or offset by pressure superposition. The appliance for the membrane electrophoresis comprises at least an at least quadrupartite separation chamber (7), having at least one diluate space (16) and one concentrate space (17) and also a cathode space (18) and an anode space (21) having electrodes as anode (19) and cathode (20), with the individual spaces (16, 17, 18, 21) being separated from each other by ultrafiltration or microfiltration membranes (14, 15); feed lines (22) and discharge lines (23) for the diluate, feed lines (24) and discharge lines (25) for the concentrate, optionally feed lines (26) and discharge lines (27) for the electrode rinsing solution, and also a device (8; 10) or (9; 11) for pressure regulation by means of which a pressure difference, in particular of at least 3 kPa, can be generated between the diluate space (16) and the concentrate space (17).

25 Claims, 2 Drawing Sheets

DEVICE AND METHOD FOR PREPARATIVE ELECTROPHORESIS

The invention relates to a method and an appliance for performing membrane electrophoresis using microfiltration or ultrafiltration membranes. In the method, the electroosmotic flow which develops in the membrane pores is reduced or compensated for by means of pressure superposition.

BACKGROUND OF THE INVENTION

The possibility of using electrophoresis as a preparative separation technique has been investigated since the nineteen fifties.

In continuous free-flow electrophoresis, a solution flows into an electrophoresis chamber and is separated in the electrical field between two electrodes. On leaving the electrophoresis module, the liquid flow is divided into a large number of fractions which contain the substances to be separated at different concentrations. Although this technique leads to good selectivities on a laboratory scale, scaling-up is only possible within narrow limits. The main problem is considered to be the heating of the solution in the electrical field and the dispersion phenomena, such as heat convection, resulting from this. Productivities of only a few grams of product per day can be achieved using commercially available free-flow electrophoresis appliances.

In membrane electrophoresis, semipermeable membranes act as convection barriers between adjacent compartments, with at least one dissolved component being able to migrate, in the electrical field, from one compartment into another.

The first publications used macroporous membranes, for example filter paper. However, these materials suffer from a number of disadvantages: they do not exhibit any selectivity for the substances to be separated (U.S. Pat. No. 3,989,613, U.S. Pat. No. 4,043,895) and, in addition to this, frequently exhibit only a low degree of mechanical and chemical stability. Moreover, they are susceptible to non-negligible pressure-induced transmembrane flows at pressure differences of less than 1 kPa. Pressure differences, which can vary temporarily or locally, between individual compartments consequently lead to backmixing and to a decrease in separation efficiency. Gritzner reduced this pressure-induced permeate flow by linking to equilibration tanks (U.S. Pat. No. 4,043,895). By means of variable levels, the hydrostatic pressures in the two flow channels adjust themselves independently to the same value.

Subsequent patents propose using ultrafiltration membranes which exhibit selectivity for macromolecules of different sizes. In theory, the separation efficiency can consequently be markedly increased by combining the selectivity criteria, electrophoretic mobility and membrane retention. Aside from laid-open specifications without any implementation example (DE 3 337 669 A1, DE 3 626 953 A1), batch experiments on only a millilitre scale have been published (U.S. Pat. No. 6,270,672).

However, very low productivity is observed in practice when using ultrafiltration membranes. An electrical double layer develops in the membrane pores, leading, in the electrical field, to the induction of an electroosmotic flow which drastically reduces the capacity to separate negatively charged proteins (Galier et al., J. Membr. Sci. 194 [2001] 117-133).

If a protein species is positively charged under separation conditions, the separation can be carried out under reversed electrode polarity. In this case, the electroosmotic flow can be in the opposite orientation to the protein transport through the membrane or in the same orientation. Correspondingly, an increase or a decrease in the level of liquid is observed in the diluate container. While productivity decreases in the first case, the second case results in a decrease in separation efficiency since proteins of low mobility, which should remain in the diluate, can be transported convectively through the membrane. It is consequently not possible to equalize liquid flows through the separation membranes by equalizing hydrostatic pressure differences in the module, as described, for example, in U.S. Pat. No. 4,043,895.

The use of gel membranes represents an alternative to using porous ultrafiltration and microfiltration membranes. This nonporous material offers the advantage of low electroosmotic flow. The selectivity of the gel membrane for macromolecules can be influenced by the degree of polymer crosslinking (cf. U.S. Pat. No. 4,243,507).

However, gel membranes suffer from a number of disadvantages as compared with porous membranes:

They exhibit high resistance in an electrical field. This leads to high energy input and consequently to the evolution of a great deal of heat in the module.

Gels such polyacrylamide possess poor pH stability and cannot therefore be cleaned like conventional ultrafiltration and microfiltration membranes. This results in very high costs for module replacement since cleaning when handling proteins is essential.

On the one hand, the use of ultrafiltration and microfiltration membranes for membrane electrophoresis has thus far been limited by the electroosmotic effect. On the other hand, while gel membranes can be used, with the above-mentioned disadvantages, scaling-up fails because of the membrane costs and energy input being too high.

The invention is based on the object of developing an improved membrane electrophoresis method which uses ultrafiltration and microfiltration membranes and which does not suffer from the disadvantages mentioned here.

Because of the electroosmotic flow which develops in porous membranes, use of these membranes on an industrial scale (>0.5 kg/h), for example, has not previously been possible.

SUMMARY OF THE INVENTION

It has now been found that the electroosmotic flow in the membranes employed, and the volume changes resulting therefrom, can be offset by superimposing a regulated hydrostatic pressure.

DETAILED DESCRIPTION

The invention relates to a method for the membrane electrophoresis of substances which are dissolved or dispersed in electrolyte-containing solution using an at least quadripartite separation chamber which possesses in each case at least one diluate space and one concentrate space and also a cathode space and an anode space possessing electrodes as the anode and the cathode, with the individual spaces being separated from each other by means of porous membranes, in particular ultrafiltration or microfiltration membranes, and the electrodes being circumcirculated by electrode rinsing solution and the diluate being continuously conducted through the diluate space, or the concentrate being continuously conducted through the concentrate space, wherein at least one substance which is dissolved or dispersed in the diluate is electrophoretically transferred, by means of an electrical field which is applied between the anode and the cathode, from the diluate space to the concentrate space, with a pressure difference of at least 3 kPa being established between the diluate space and the concentrate space.

Preference is given to a a pressure difference between the diluate space and the concentrate space which is adjusted such that any liquid flow through the separation membrane which separates the concentrate space and the diluate space from each other is essentially prevented.

Preference is given to the method being carried out in a separation chamber which comprises in each case several diluate spaces and concentrate spaces, with the diluate spaces and concentrate spaces being arranged alternately between the anode space and the cathode space, which spaces are separated from each other by means of ultrafiltration and/or microfiltration membranes and are operated while being connected in parallel and/or in series.

In a preferred embodiment, the diluate liquid, the concentrate liquid and the electrode washing solution, or one or other of these solutions, is/are, independently of each other, temperature-controlled, preferably cooled.

The porous membranes have a pore size of from 1 to 1,000 nm, in particular.

The membranes are preferably based on one or more of the following materials: cellulose ester, polyacrylonitrile, polyamide, polyether, polyethersulphone, polypropylene, polysulphone, polyvinyl alcohol, polyvinylidene fluoride or aluminium oxide, silicon oxide, titanium oxide or zirconium oxide, and also ceramics composed of the abovementioned oxides.

Particular preference is given to an embodiment in which the anode space and the cathode space are flushed through with electrode rinsing solution, independently of each other.

The electrolytes which are used for the diluate solution, the concentrate solution and the electrode rinsing solution preferably contain a combination of weak acids and weak bases, weak acids and strong bases or strong acids and weak bases.

Particular preference is given to the electrolytes containing one or more of the following compounds:

boric acid, phosphoric acid, N-2-(acetamido)-2-aminoethanesulphonic acid, N-2-(acetamido)iminodiacetic acid, alanine, 2-amino-2-methyl-1,3-propanediol, ammonia, N,N-bis(2-hydroxyethyl)-2-aminoethanesulphonic acid, N,N-bis-(2-hydroxyethyl)glycine, 2,2-bis(hydroxyethyl) iminotris(hydroxymethyl)methane, 2-(cyclohexylamino) ethanesulphonic acid, acetic acid, glycine, glycylglycine, 2-[4-(2-hydroxyethyl)-1-piperazinyl]ethanesulphonic acid, 3-[4-(2-hydroxyethyl)-1-piperazinyl]propanesulphonic acid, histidine, imidazole, lactic acid, 2-morpholinoethanesulphonic acid, 2-morpholinopropanesulphonic acid, piperazine-1,4-bis(2-ethanesulphonic acid), N-[tris (hydroxymethyl)methyl]-2-aminoethanesulphonic acid, N-[tris(hydroxymethyl)methyl]glycine, triethanolamine, tris(hydroxymethyl)amino-methane and citric acid.

Based on the membrane area, the current density is preferably from 10 to 1,000 $A/m^2$, in particular from 10 to 500 $A/m^2$.

The conductivity of the diluate solution is preferably from 0.1 mS/cm to 40 mS/cm, in particular from 0.1 to 10 mS/cm.

Preference is also given to an embodiment in which the conductivity of the diluate solution is lowered during the separation.

In a further advantageous embodiment the diluate solution is concentrated after the separation, in particular by means of combination with a liquid permeation, such as microfiltration, ultrafiltration, nanofiltration or reverse osmosis, and returned to the diluate space again.

The method can in particular be used for one or more of the following substances: proteins, peptides, DNA, RNA, oligo-nucleotides, oligosaccharides, polysaccharides, viruses, viral constituents, cells, cell constituents, enantiomers and diastereomers.

The invention furthermore relates to an appliance for the membrane electrophoresis which at least comprises an at least quadripartite separation chamber which possesses at least one diluate space and one concentrate space and also a cathode space and an anode space having electrodes as the anode and the cathode, with the individual spaces being separated from each other by means of porous membranes, in particular by means of ultrafiltration or microfiltration membranes, feed lines and discharge lines for a diluate, feed lines and discharge lines for the concentrate, where appropriate feed lines and discharge lines for the electrode washing solution, and also a device for pressure regulation by means of which a pressure difference, in particular of at least 3 kPa, can be produced between diluate space and concentrate space.

Preference is given to the separation chamber being subdivided into several diluate spaces and concentrate spaces.

Several diluate spaces and concentrate spaces, which are separated from each other by means of porous restriction membranes or separation membranes and which are preferably connected in parallel and/or in series, are preferably arranged alternately between the anode space and the cathode space.

Preference is furthermore given to an appliance in which feed lines and discharge lines for the diluate are arranged in a diluate circuit, feed lines and discharge lines for the concentrate are arranged in a concentrate circuit and, where appropriate, feed lines and discharge lines for the electrode rinsing solution are arranged in an electrode rinsing circuit.

Preference is likewise given to an appliance which possesses a diluate circuit, a concentrate circuit and an electrode rinsing circuit and, in particular, possesses heat exchangers in one or other or all of these circuits.

In a preferred variant, the electrode rinsing circuit is formed by a separate anode rinsing circuit and cathode rinsing circuit.

The electroosmotic flow can be offset by pressure superposition in individual pressure-proof vessels. The pressure difference can be from a few kPa up to a few 100 kPa.

The pressure superposition can also be created by regulating the pump pressures or the pump volume flows.

Alternatively, an indirect regulation can be effected by adjusting the volume flows at inlets and outlets of the membrane electrophoresis module to identical values.

The device is suitable for purifying dissolved or dispersed substances in aqueous medium. Application examples are the purification of proteins, peptides, DNA, RNA, oligosaccharides, polysaccharides, oligonucleotides, viruses, cells and chiral molecules.

The method is particularly suitable for purifying proteins, peptides, oligonucleotides oligosaccharides, polysaccharides and virus particles.

The invention therefore also relates to the use of the appliance according to the invention for purifying proteins, peptides, DNA, RNA, oligonucleotides, viruses, cells or chiral molecules.

The invention can be applied both in a batch operation as in a continuous mode.

BRIEF DESCRIPTION OF THE DRAWINGS

Using the figures, the invention is explained in more detail below by means of the examples, which do not, however, constitute any restriction of the invention.

EXAMPLES

Figure 1:
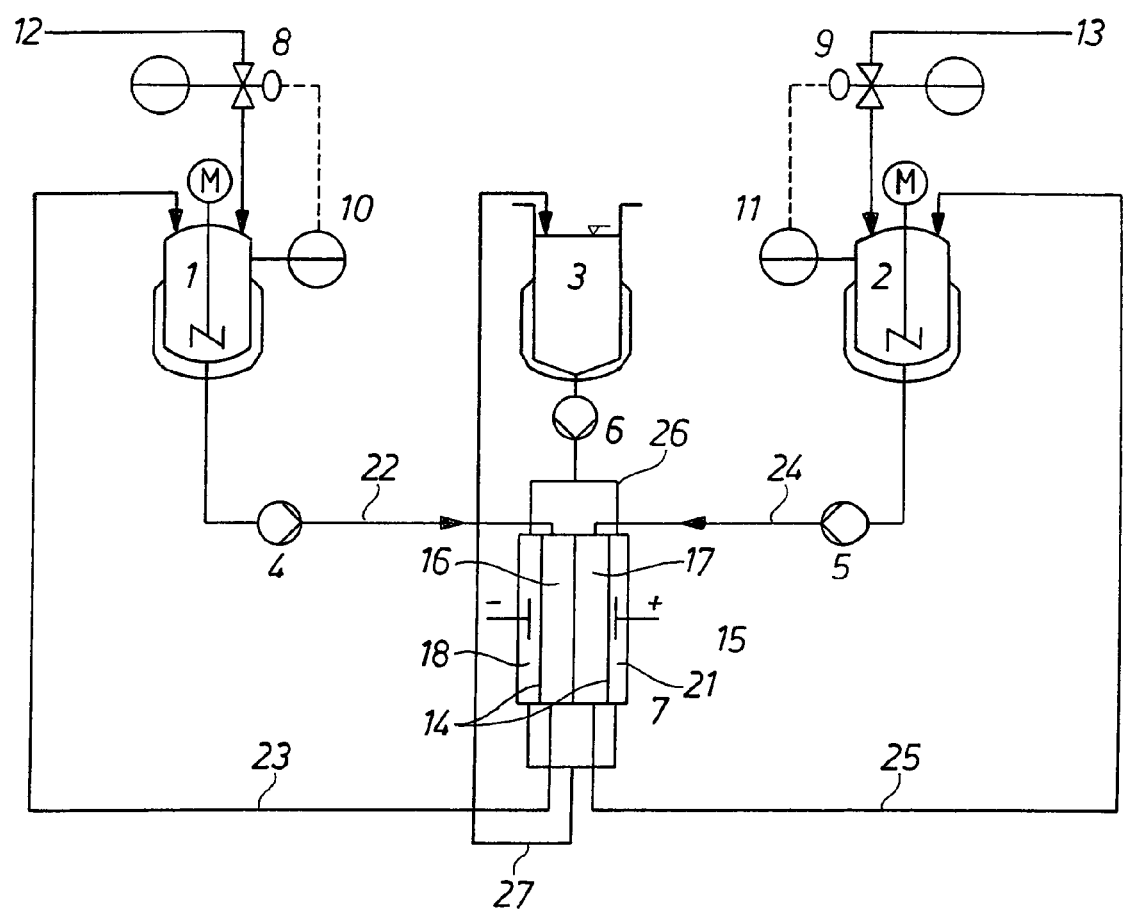
FIG. 1 shows a diagram of a membrane electrophoresis unit possessing a device for pressure superposition

The unit (FIG. 1) which is used in the examples described below is comprised of in each case one temperature-controllable recipient vessel for diluate 1, concentrate 2 and electrode buffer 3. The solutions are recirculated by means of pumps 4, 5, 6 by way of forward feed lines 22, 24, 26 and return lines 23, 25, 27 and flow through an electrophoresis separation module 7. The pressure superposition in the gas space of the diluate container and the concentrate container with nitrogen from lines 12, 13 is effected by means of back pressure controllers 8, 9. The back pressure controllers are in turn regulated by way of level probes 10, 11.

The membrane electrophoresis unit contains a module 7a (compare FIG. 2) containing in each case four parallel diluate spaces 16a-d and concentrate spaces 17a-d. Liquid flows in parallel into the diluate spaces 16a-d and concentrate spacers 17a-d by way of liquid distributors 28, 29 and the spaces are delimited by restriction membranes 14 and separation membranes 15. The diluate spaces and concentrate spaces can contain grids or fabrics (not shown here) which function as spaces between the membranes and as flow breakers. Liquid flows into the electrode spaces 18, 21 in parallel and the electrode spaces are delimited by restriction membranes 14. An electrical field is created by way of electrodes 19, 20. The electrical field can be set up either with the polarity shown in FIG. 2, or with the opposite polarity.

Example 1

Figure 2:
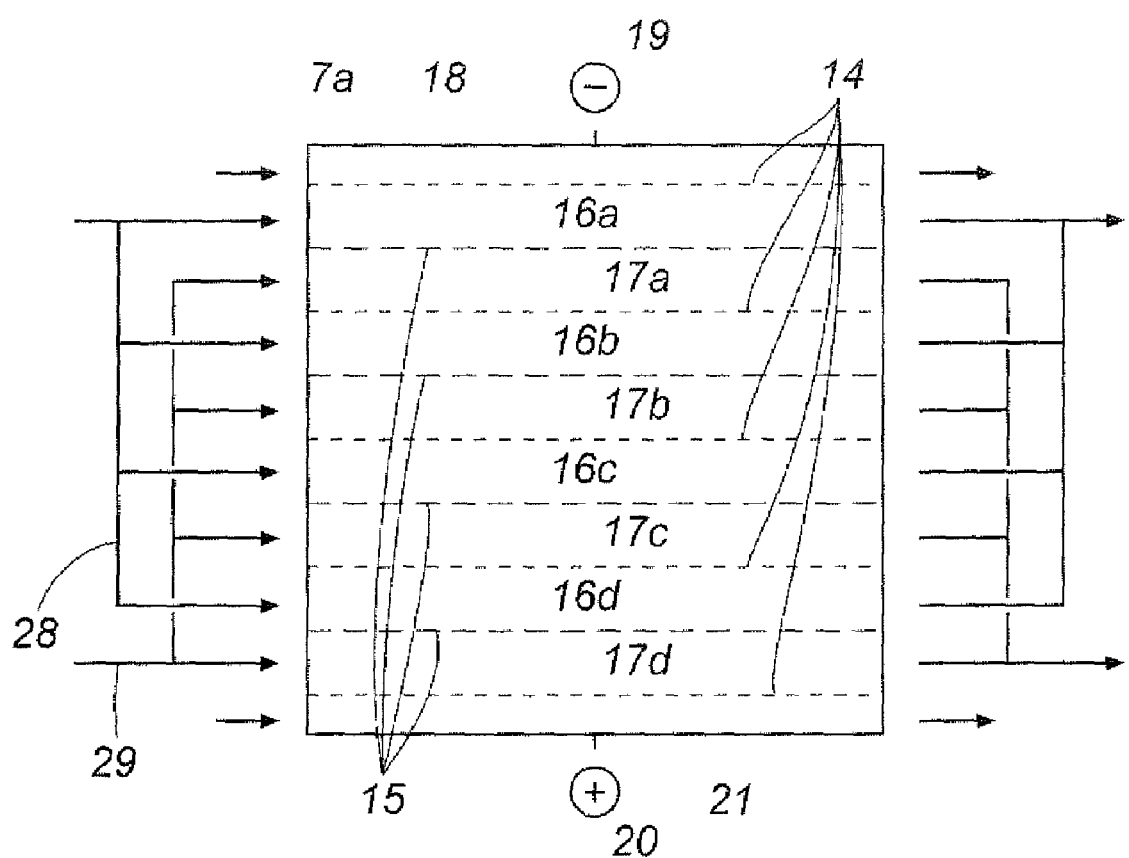
FIG. 2 shows a diagram of a membrane electrophoresis module (quadruple stack)

The unit shown in FIG. 1 and the module 7a sketched in FIG. 2 were used for separating human serum albumin (HSA) from human immunoglobulin G (IgG). Module 7a was a modified electrodialysis module ED 136 from FuMA-Tech GmbH) having an effective membrane area of 36 cm$^2$ per membrane layer.

A HEPES(2-[4-(2-hydroxyethyl)-1-piperainyl]ethane sulphonic acid)imidazole buffer was used (approx. 40 mM HEPES/15 mM imidazole, pH 7). The recipient vessels for concentrate solution 2 and electrode rinsing solution 3 were in each case filled with 1,000 mL of a buffer solution. The diluate recipient vessel was filled with 400 mL of buffer in which HSA and IgG were dissolved at concentrations of 38 g/L and 4.5 g/L, respectively.

Restriction membranes 14 having a nominal cutoff point of 10 kDa and separation membranes 15 having a nominal cutoff point of 300 kDa were assembled, using standard spacers (from FuMA-Tech GmbH), into a quadruple stack. The membranes which were used were SARTORIUS® PES polyethersulphone ultrafiltration membranes.

The experiment was carried out at a current density of about 45 A/m$^2$, with a negative potential being applied to the diluate-side electrode 20. The volume flows in the diluate circuit and concentrate circuit were in each case 320 ml/min, while the volume flow in the electrode circuit was 700 ml/min. The protein concentrations were determined by means of HPLC analysis.

The following experiments were carried out:
1a) electrophoresis with compensation for the electroosmotic flow by using pressurization to regulate the level in the diluate recipient vessel 1b) electrophoresis without compensation for the electroosmotic flow.

Table 1 contains experimental parameters and concentration trends for experiment 1a while Table 2 contains the data for experiment 1b. Experiment 1b had to be terminated after 180 minutes since the diluate recipient vessel had become completely full.

The decrease in the concentration of albumin in the diluate is concentration-dependent and follows a first-order kinetics of the form:

$$\frac{dc}{dt} \cdot \frac{V}{A} = -k \cdot c$$

where
  c: albumin concentration in the diluate [g/L]
  t: time [h]
  V: volume of diluate [L]
  A: effective area of separation membranes [m$^2$]
  k: rate constant [L/(hm$^2$)]
Integrating and solving for the residual fraction gives:

$$\ln\left(\frac{c}{c_0}\right) \cdot \frac{V}{A} = -k \cdot t$$

where $c/c_0$: residual fraction [−]

If account is taken of the fact that the diluate volume is not absolutely constant, an effective rate constant can be calculated by using the protein masses instead of the concentrations:

$$\ln\left(\frac{m}{m_0}\right) \cdot \frac{V}{A} = -k_{\mathit{eff}} \cdot t$$

where
  m: albumin mass in the diluate [g]
  $m_0$: albumin mass in the diluate at the beginning of the [g]experiment
  $m/m_0$: mass-based residual fraction [−]
  $k_{\mathit{eff}}$: effective rate constant [L/(h/m$^2$)]

Mass-related residual fractions of 0.45 (Experiment 1a) and 0.64 (Experiment 1b), respectively, are obtained after 180 minutes for the depletion of serum albumin. If these values are inserted into the above-described formula, the effective rate constant which is then obtained for Example 1a is 1.8 times that obtained for Example 1b. Depletion therefore takes place almost twice as fast when pressure compensation is employed.

The selectivity of the depletion is calculated as follows:

$$\psi = \frac{\ln[m/m_0(\mathrm{HSA})]}{\ln[m/m_0(\mathrm{IgG})]}$$

where
  Ψ: Selectivity [−]
  $m/m_0$ (HSA): mass-based residual fraction of HSA in the diluate [−]
  $m/m_0$ (IgG): mass-based residual fraction of IgG in the diluate [−]

A selectivity of 8.8 is obtained over the entire course of Experiment 1a whereas only a selectivity of 3.8 is achieved in Experiment 1b.

Example 2

The unit shown in FIG. 1 and the module 7a sketched in FIG. 2 were used for separating human serum albumin from haemoglobin. The module 7a was a modified electrodialysis module as in Example 1 having an effective membrane area of 36 cm$^2$ per membrane layer.

50 millimolar MES/hisitidine buffer was used (approx. 15 mM MES/35 mM histidine, pH 6.5). The recipient vessels for concentrate solution 2 and electrode rinsing solution 3 were filled with 1 L and 800 mL of buffer solution, respectively. The diluate recipient vessel 1 contained the two proteins dissolved in buffer at mass concentration of 4.5 g/L of human serum albumin and 0.85 g/L of haemoglobin. The volume of the diluate liquid was 400 mL and was kept constant during the experiment by means of pressure superposition.

Restriction membranes 14 having a nominal cutoff point of 10 kDa and separation membranes 15 having a nominal cutoff point of 300 kDa were assembled, using standard spacers as in Example 1, into a quadruple stack. The membranes which were used were SARTORIUS® PES ultrafiltration membranes.

The experiment was carried out at a current density of 45 A/m$^2$, with a negative potential being applied to the diluate-side electrode 20. The volume flows in the diluate circuit and the concentrate circuit were in each case 160 mL/min while the volume flow in the electrode circuit was 770 mL/min. The protein concentrations were determined by means of HPLC analysis. The levels in the recipient vessels were kept constant by concentrate-side pressure regulation.

After 3 h, a 92% depletion of the human serum albumin had been achieved in the diluate while the yield of haemoglobin in the diluate was 83%. The course of the experiment is shown in Table 3.

TABLE 1

Results of the HSA/IgG separation (Example 1a).

| Time/min | Gas pressure/kPa (diluate space) | Volume/mL (diluate) | Current density/A/m$^2$ | m (HSA)/g (diluate) | m (IgG)/g (diluate) |
|---|---|---|---|---|---|
| 0 | 0 | 439 | 45 | 14.3 | 1.6 |
| 30 | 0 | 451 | 47 | 12.5 | 1.6 |
| 60 | 9 | 451 | 47 | 10.9 | 1.5 |
| 90 | 14 | 462 | 45 | 10.0 | 1.5 |
| 120 | 15 | 462 | 45 | 8.6 | 1.4 |
| 150 | 18 | 466 | 42 | 7.5 | 1.3 |
| 180 | 20 | 474 | 50 | 6.5 | 1.3 |
| 210 | 21 | 474 | 45 | 5.7 | 1.3 |
| 240 | 20 | 474 | 45 | 4.9 | 1.3 |
| 270 | 23 | 482 | 42 | 4.2 | 1.3 |
| 300 | 24 | 466 | 45 | 3.3 | 1.4 |
| 330 | 21 | 474 | 42 | 2.7 | 1.3 |
| 360 | 22 | 462 | 42 | 2.4 | 1.3 |

TABLE 2

Results of the HSA/IgG separation (Example 1b).

| Time/min | Gas pressure/kPa (diluate space) | Volume/mL (diluate) | Current density/A/m$^2$ | m (HSA)/g (diluate) | m (IgG)/g (diluate) |
|---|---|---|---|---|---|
| 0 | 0 | 423 | 45 | 13.8 | 1.8 |
| 30 | 0 | 470 | 42 | 12.9 | 1.6 |
| 60 | 0 | 520 | 45 | 11.5 | 1.3 |
| 90 | 0 | 602 | 40 | 10.2 | 1.5 |
| 120 | 0 | 684 | 42 | 9.3 | 1.2 |
| 150 | 0 | 750 | 42 | 9.7 | 1.7 |
| 180 | 0 | 820 | 42 | 8.8 | 1.6 |

TABLE 3

Results of the HSA/haemoglobin separation (Example 2).

| Time/min | Gas pressure/kPa (diluate space) | Volume/mL (diluate) | Current density/A/m$^2$ | m (HSA)/g (diluate) | m (haem)/g (diluate) |
|---|---|---|---|---|---|
| 0 | 0 | 420 | 45 | 1.85 | 0.35 |
| 30 | 4 | 420 | 45 | 1.29 | 0.34 |
| 60 | 6 | 420 | 47 | 0.79 | 0.32 |
| 90 | 3 | 420 | 45 | 0.48 | 0.31 |
| 120 | 5 | 420 | 45 | 0.30 | 0.30 |
| 150 | 3 | 420 | 45 | 0.20 | 0.29 |
| 180 | 7 | 420 | 42 | 0.14 | 0.29 |

We claim:

1. Method for the membrane electrophoresis of substances which are dissolved or dispersed in electrolyte-containing solution using an at least quadrupartite separation chamber (7) which comprises at least one pair of diluate spaces (16) and concentrate spaces (17), a cathode space (18) and an anode space (21) having electrodes as anode (19) and cathode (20), the diluate spaces and concentrate spaces of each pair being separated from each other by ultrafiltration or microfiltration membranes (15); the cathode space and anode space being separated from the pairs of diluate and concentrate spaces by restriction membranes and each pair of diluate and concentrate spaces, if there be more than one, being separated from the others by restriction membranes, said separation chamber also comprising an electrode rinsing solution being circulated through the electrode spaces (18, 21), and, diluate being continuously conducted through the diluate space (16), and, respectively, a concentrate being continuously conducted through the concentrate space (17), wherein at least one substance which is dissolved or dispersed in the diluate is transferred electrophoretically, by means of an electrical field which is applied between the anode (19) and the cathode (20), from the diluate space (16) to the concentrate space (17), with a pressure difference of at least 3 kPa being maintained between the diluate space (16) and the concentrate space (17) of each pair of diluate spaces and concentrate spaces.

2. Method according to claim 1, wherein the pressure difference maintained between the diluate space (16) and the concentrate space (17) is a pressure difference sufficient to essentially prevent any liquid flow through the separation membrane (15) which separates the concentrate space (17) and the diluate space (16) from each other.

3. Method according to claim 1, wherein the separation chamber (7) comprises a separation module (7a) which is comprised of several pairs of diluate spaces (16a, 16b, ...) and concentrate spaces (17a, 17b, ...) which are operated in parallel and/or in series.

4. Method according to claim 1, wherein the diluate liquid, the concentrate liquid and the electrode rinsing solution, or any one of these solutions, is/are temperature-controlled.

5. Method according to claim 4, wherein at least two of said diluate liquid, concentrate liquid and electrode rinsing solution are temperature-controlled, and each is temperature-controlled independently of the other(s).

6. Method according to claim 4, wherein said temperature-control comprises cooling.

7. Method according to claim 1, wherein the ultrafiltration or microfiltration membranes have a pore size of from 1 to 1,000 nm.

8. Method according to claim 7, wherein the ultrafiltration or microfiltration membranes are formed of a material selected from the group consisting of cellulose ester, polyacrylonitrile, polyamide, polyether, polyethersulphone, polypropylene, polysulphone, polyvinyl alcohol, polyvinylidene fluoride, aluminum oxide, silicon oxide, titanium oxide, zirconium oxide, and ceramics comprised of one or more of the abovementioned oxides.

9. Method according to claim 1, wherein electrode rinsing solution is passed through the anode space (21) and the cathode space (18) independently of each other.

10. Method according to claim 1, wherein the diluate solution, the concentrate solution and the electrode rinsing solution comprise electrolytes which are combinations of weak acids and weak bases, weak acids and strong bases or strong acids and weak bases.

11. Method according to claim 10, wherein the electrolytes comprise one or more compounds selected from the group consisting of boric acid, phosphoric acid, N-2-(acetamido)-2-aminoethauesulphonic acid, N-2-(acetamido)iminodiacetic acid, alanine, 2-amino-2-methyl-1,3-propanediol, ammonia, N,N-bis(2-hydroxyethyl)-2-aminoethanesulphonic acid, N,N-bis(2-hydroxyethyl)glycine, 2,2-bis(hydroxyethyl)iminotris(hydroxymethyl)methane, 2-cyclo-hexylamino (ethanesulphonic acid), acetic acid, glycine, glycyiglycine, 2-[4-(2-hydroxyethyl)-1-piperazinyl]ethanesulphonic acid, 3-[4-(2-hydroxyethyl)-1-piperazinyl]propanesulphonic acid, histidine, imidazole, lactic acid, 2-morpholinoethanesulphonic acid, 2-morpholinopropanesulphonic acid, piperazine-1,4-bis(2-ethanesulphonic acid), N-[tris(hydroxymethyl)methyl]-2-aminoethanesuiphonic acid, N-[tris (hydroxymethyl)methyl]glycine, triethanolamine, tris (hydroxymethyl)aminomethane and citric acid.

12. Method according to claim 1, wherein the current density, based on the area of the individual ultrafiltration or microfiltration membranes, is from 10 to 1,000 A/m$^2$.

13. Method according to claim 12, wherein said current density is from 10 to 500 A/m$^2$.

14. Method according to claim 1, wherein the conductivity of the diluate solution is from 0.1 mS/cm to 40 mS/cm.

15. Method according to claim 14, wherein said conductivity is from 0.1 to 10 mS/cm.

16. Method according to claim 1, wherein the conductivity of the diluate solution is lowered during the separation.

17. Method according to claim 1, wherein, after the separation, the diluate solution is concentrated by microfiltration, ultrafiltration, nanofiltration or reverse osmosis, and returned to the diluate space (16).

18. Method according to claim 1, wherein said substance is selected from the group consisting of proteins, peptides, DNA, RNA, oligonucleotides, oligosaccharides, polysacoharides, viruses, virus constituents, cells, cell constituents, enantiomers, diastereomers and combinations thereof, 19. Appliance for membrane electrophoresis, comprising an at least quadrupartite separation chamber (7) said separation chamber comprising a plurality of pairs of diluate spaces (16) and concentrate spaces (17), a cathode space (18) and an anode space (21) having electrodes as anode (19) and cathode (20), with the diluate space and concentrate space of each pair being separated from each other by ultrafiltration or microfiltration membranes (15); the cathode space and anode space being separated from the pairs of diluate and concentrate spaces by restriction membranes and each pair of diluate and concentrate spaces being separated from the others by restriction membranes, said appliance also comprising feed lines (22) and discharge lines (23) for diluate, feed lines (24) and discharge lines (25) for concentrate, optionally feed lines (26) and discharge lines (27) for an electrode washing solution, and also a pressure regulation system (8; 10) or (9; 11) for generating a pressure difference of at least 3 kPa between the diluate spaces (16) and the concentrate spaces (17), said restriction membranes having substantially lower cutoff points than said ultrafiltration or microfiltration membranes.

20. Appliance according to claim 19, wherein the pairs of diluate spaces and concentrate spaces are connected to each other in parallel and/or in series, and are arranged alternately between the anode space (21) and the cathode space (18).

21. Appliance according to claim 19, wherein feed lines (22) and discharge lines (23) for the diluate are arranged in a diluate circuit (1; 4; 22; 23), feed lines (24) and discharge lines (25) for the concentrate are arranged in a concentrate circuit (2; 5; 24; 25) and, optionally, feed lines (26) and discharge lines (27) for the electrode rinsing solution are arranged in an electrode rinsing circuit (3; 6; 26; 27).

22. Appliance according to claim 21 comprising heat exchangers in one or more of said circuits.

23. Appliance according to claim 21, wherein the electrode rinsing circuit comprises a separate anode rinsing circuit and cathode rinsing circuit.

24. Appliance according to claim 19, wherein said membranes have a pore size of from 1 to 1,000 nm.

25. Appliance according to claim 19, wherein the membranes are formed of a material selected from the group consisting of cellulose ester, polyacrylonitrile, polyamide, polyether, polyethersulphone, polypropylene, polysulphone, polyvinyl alcohol, polyvinylidene fluoride, aluminum oxide, silicon oxide, titanium oxide, zirconium oxide and ceramics comprised of the above mentioned oxides.

* * * * *